US011103715B2

(12) United States Patent
Fort (10) Patent No.: US 11,103,715 B2
(45) Date of Patent: Aug. 31, 2021

(54) DEVICES AND METHODS FOR CHARGING MEDICAL DEVICES

(71) Applicant: COCHLEAR LIMITED, Macquarie University (AU)

(72) Inventor: Andrew David Fort, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 1314 days.

(21) Appl. No.: 14/318,256

(22) Filed: Jun. 27, 2014

(65) Prior Publication Data

US 2015/0380972 A1 Dec. 31, 2015

(51) Int. Cl.

| H02J 7/00 | (2006.01) |
|---|---|
| A61N 1/378 | (2006.01) |
| H02J 50/10 | (2016.01) |
| H02J 50/40 | (2016.01) |
| H02J 50/80 | (2016.01) |
| H02J 50/50 | (2016.01) |
| A61N 1/36 | (2006.01) |
| A61N 1/05 | (2006.01) |

(52) U.S. Cl.
CPC ....... *A61N 1/3787* (2013.01); *A61N 1/36038* (2017.08); *H02J 50/10* (2016.02); *H02J 50/40* (2016.02); *H02J 50/50* (2016.02); *H02J 50/80* (2016.02); *A61N 1/0541* (2013.01); *A61N 1/36125* (2013.01)

(58) Field of Classification Search
CPC ......... Y02E 60/12; H02J 7/025; H02J 7/0042; H01F 38/14; Y02T 90/122; B60L 11/182; B60L 53/12; B60L 53/20; B60L 53/122

USPC .................................. 320/108, 107; 307/104
See application file for complete search history.

(56) References Cited

U.S. PATENT DOCUMENTS

| 5,702,431 A * | 12/1997 | Wang ................... A61N 1/3787 607/33 |
|---|---|---|
| 8,751,001 B2 | 6/2014 | Grevious et al. |
| 2004/0185826 A1* | 9/2004 | Koskinen .............. H04M 15/00 455/406 |
| 2008/0146185 A1* | 6/2008 | Van Zeijl ............... H04B 1/005 455/313 |
| 2009/0039828 A1* | 2/2009 | Jakubowski ............ H02J 7/342 320/106 |
| 2010/0201201 A1* | 8/2010 | Mobarhan ............... H02J 5/005 307/104 |
| 2013/0095758 A1* | 4/2013 | Baarman ................... A61L 2/10 455/41.1 |
| 2013/0099735 A1* | 4/2013 | Partovi ................. H01F 7/0252 320/108 |
| 2013/0241478 A1* | 9/2013 | Azancot .................. H01F 38/14 320/108 |
| 2013/0335020 A1* | 12/2013 | Moore ..................... H02J 7/025 320/109 |

(Continued)

*Primary Examiner* — Richard Isla
*Assistant Examiner* — Mohammed J Sharief
(74) *Attorney, Agent, or Firm* — Edell, Shapiro & Finnan, LLC (57) ABSTRACT

Devices and methods are used to bridge between standard wireless charging protocols and proprietary wireless charging protocols utilized in auditory prostheses. Such devices are portable and can enable a recipient to charge her device whenever wireless power is available. Additionally, the recipient can change settings on her prosthesis, via the bridge device, while her prosthesis is charging.

19 Claims, 8 Drawing Sheets

(56) References Cited

U.S. PATENT DOCUMENTS

| | | | |
|---|---|---|---|
| 2014/0103865 A1* | 4/2014 | Van Wiemeersch et al. ............... 320/108 | |
| 2014/0183962 A1* | 7/2014 | Qian ................ | H02J 7/025 307/104 |
| 2014/0266034 A1* | 9/2014 | Lee .................. | H02J 7/025 320/108 |
| 2014/0285008 A1* | 9/2014 | Azancot ............ | H01F 38/14 307/24 |
| 2014/0354223 A1* | 12/2014 | Lee .................. | H02J 7/025 320/108 |
| 2015/0015194 A1* | 1/2015 | Leabman ........... | H04B 1/04 320/108 |
| 2015/0028800 A1* | 1/2015 | Kim .................. | H02J 7/025 320/108 |
| 2015/0091496 A1* | 4/2015 | Meunier ............ | H02J 7/025 320/106 |

* cited by examiner

DEVICES AND METHODS FOR CHARGING MEDICAL DEVICES

BACKGROUND

An auditory prosthesis often includes an implantable portion having a stimulating assembly and an external portion having speech processing hardware and software, as well as a battery. The battery provides power to the external portion so as to enable the appropriate signals to be sent to the implantable portion. Charging the external portion (as well as the implantable portion, if a battery is located therein) can be inconvenient, since the wireless charging protocol used for such devices is proprietary to the auditory prosthesis manufacturer. Thus, standard wireless charging stations available in many public locations (airports, cafes, etc.) are not a viable source of power for a recipient of an auditory prosthesis.

SUMMARY

Embodiments disclosed herein relate to devices and methods that are used to bridge between standard wireless charging protocols and proprietary wireless charging protocols. Such a bridge device receives power via a first induction device in the form of a standard wireless protocol, then converts that power to a different, often proprietary, wireless protocol and transmits the converted power through a second induction device to a portable device such as an auditory prosthesis. The bridge device also includes accessories that can be used to charge the battery of a fully-implanted hearing prosthesis. The bridge device is portable and can include a battery for charging when building power is unavailable. When charging with battery power, the bridge device converts power from the batteries into the proprietary wireless protocol and transmits it to the auditory prosthesis.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

In certain cases, the same number represents the same element or same type of element in all drawings.

DETAILED DESCRIPTION

Figure 1:
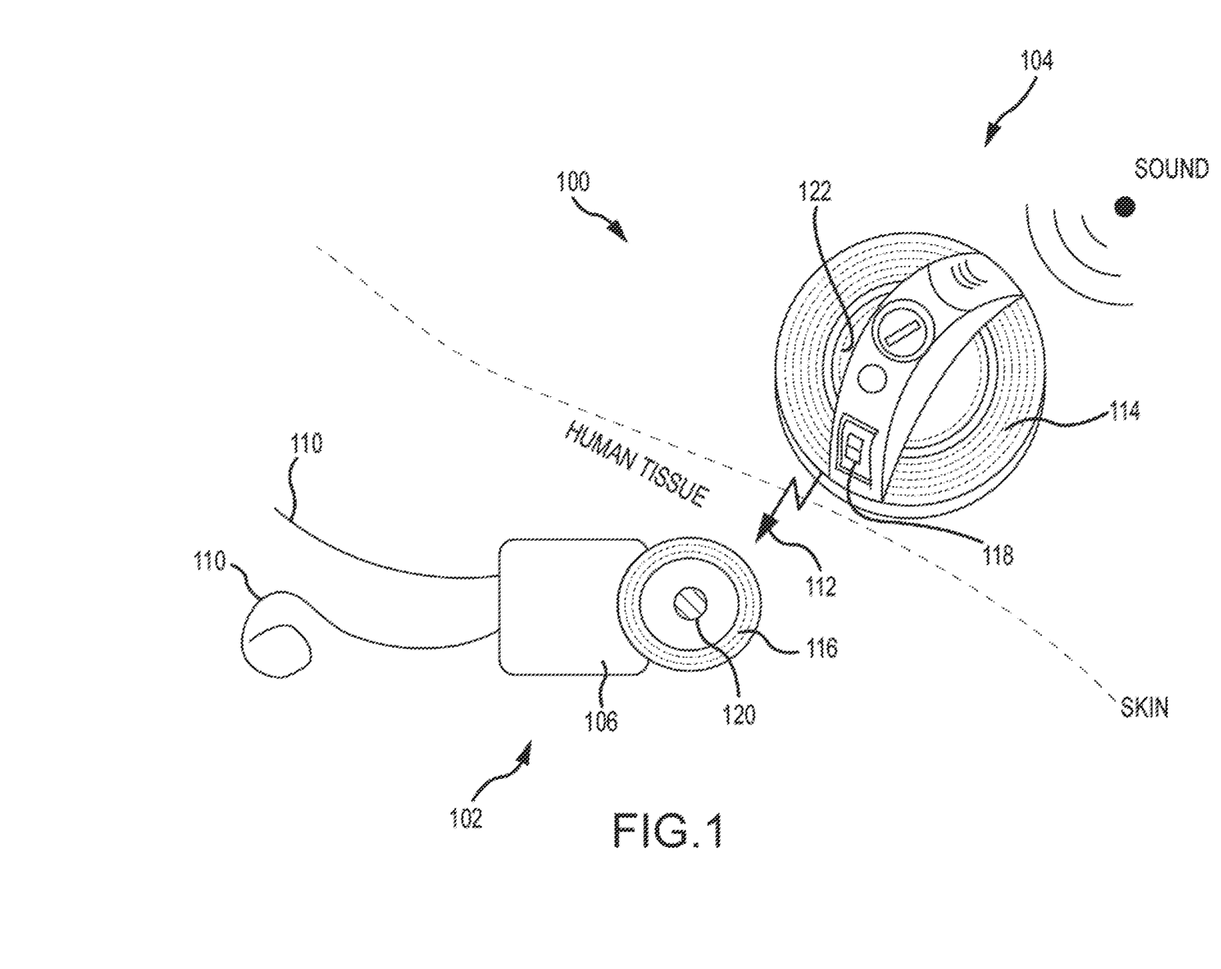
FIG. 1 is a schematic perspective view of an embodiment of an auditory prosthesis, including an implantable portion and an external portion.

While the technologies disclosed herein have particular application in the cochlear implant devices depicted in FIG. 1, it will be appreciated that the devices and methods disclosed can be employed to charge the batteries of other types of hearing prostheses. For example, the embodiments disclosed herein can be used to charge the batteries of traditional hearing aids, active transcutaneous bone conduction devices, passive transcutaneous bone conduction devices, middle ear stimulating hearing prostheses, inner ear stimulating hearing prostheses, totally-implantable auditory prostheses, or other portable or implanted prostheses that utilize a battery. Furthermore, the embodiments disclosed herein can be utilized to charge medical devices other than hearing prostheses, where a battery is utilized in conjunction with an implantable device, or where an implanted medical device includes a battery. The technologies disclosed herein will be described generally in the context of external portions of medical devices where the external portions contain batteries. Certain aspects of the technology however, for example, the external portions of a cochlear implant identified in FIG. 1, are described in the context of auditory prostheses.

FIG. 1 is a schematic perspective view of an embodiment of an auditory prosthesis 100, in this case, a cochlear implant, including an implantable portion 102 and an external portion 104. The implantable portion 102 of the cochlear implant includes a stimulating assembly 106 implanted in a body (specifically, proximate and within the cochlea 108) to deliver electrical stimulation signals to the auditory nerve cells, thereby bypassing absent or defective hair cells within the cochlea. The electrodes 110 of the stimulating assembly 106 stimulate the auditory nerve to generate a hearing precept.

The external portion 104 includes a processor that detects external sound and converts the detected sound into a coded signal 112 through a suitable sound processing strategy. The coded signal 112 is sent to the implanted stimulating assembly 106 via a transcutaneous link. In one embodiment, the signal 112 is sent from a coil 114 located on the external portion 104 to a coil 116 on the implantable portion 102. The stimulating assembly 106 processes the coded signal 112 to generate a series of stimulation sequences which are then applied directly to the auditory nerve via the electrodes 110 positioned within the cochlea. The external portion 104 also includes a battery and a status indicator 118, the functionality of which is described below. Permanent magnets 120, 122 are located on the implantable portion 102 and the external portion 104, respectively. Other embodiments of cochlear implants include totally-implantable cochlear implants, where an implantable portion contains a battery. In such devices, an external portion having a number of control components can be placed proximate to the location of the implanted portion to change settings, adjust volume, etc.

Figure 2A:
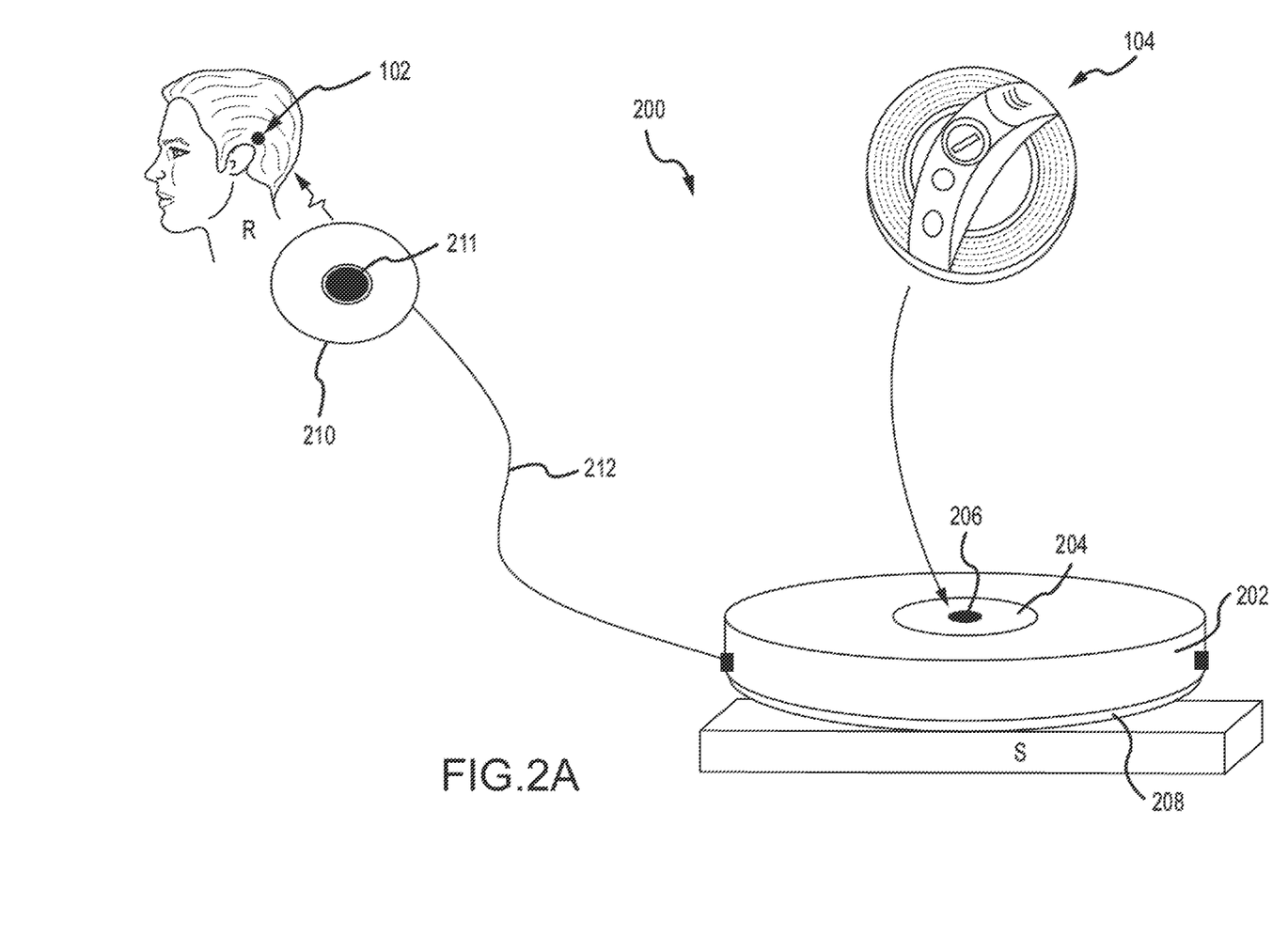
FIG. 2A is a schematic diagram of an embodiment of a bridge device used to wirelessly charge an auditory prosthesis.

FIG. 2A is a schematic diagram of an embodiment of a bridge device 200 used to wirelessly charge an auditory prosthesis. Such a bridge device 200 is used for recharging of the battery of an external portion 104 via wireless power or energy transfer with the bridge device 200 (e.g., over inductive coupling). Additionally, the bridge device 200 can include other accessories to enable charging of a battery of an implanted portion 102 while still implanted in a recipient R. Additionally, a battery of a completely implanted device (e.g., a totally implanted cochlear implant, middle ear prosthesis, or bone conduction prosthesis) can also be charged with the bridge device 200. Charging occurs over the same devices (e.g., coils) that provide power and data transfer between the implantable portion 102 and the external portion 104 of an auditory prosthesis. The bridge device 200 includes a housing 202 and a number of interfaces having induction devices located therein. In the depicted embodiment, a portable device interface 204 is defined by a target sized to match the external portion 104, which makes it easy for a recipient to understand where to locate the external portion 104 for proper charging. In certain embodiment, the target can be a shape to match the coil 114 of the external portion 104 (e.g., circular, oval, D-shaped, etc.). The portable device interface 204 can also include a magnet 206 to help locate the external portion 104 on the housing 202. The portable device interface 204 can have any form factor as required or desired for a particular application. In certain embodiments, the portable device interface 204 is a recessed or raised portion of the housing 202, configured to mate with the external portion 104. The charging bridge 200 also includes a station interface 208 that, during use, is placed proximate a wireless charging station S that emits a standard charging protocol from the station's own induction device.

The bridge device 200 can also include a remote interface 210 connected to the housing 202 (and components therein) with a cable 212. In another embodiment, the remote interface 210 can be in wireless communication with the housing 202. The remote interface 210 is configured similar to the portable device interface 204, in that it includes an induction device sized for a corresponding induction device on the implanted portion 102 of the auditory prosthesis. Additionally, the remote interface 210 can include a magnet for locating the remote interface 210 with the implantable portion 102. The various induction devices disposed at each interface (portable device 204, station 208, and remote 210) can be any type of interface used in the wireless transfer of data, power, or other signals. These can include coils, inductive surfaces, combinations of such elements, and/or any other type of interface or other arrangement of components known to the art. Typically, the induction devices are selected, sized, and shaped to match the inductive devices with which they are configured to mate. For example, the induction device located at the station interface 208 is often physically larger than the induction device located at the portable device interface 204. This is because the mating induction device on the wireless charging station S is typically larger than the induction device utilized in an external portion 104 of an auditory prosthesis. In some cases, the induction device of the portable device interface 204 can be small enough to fit within the physical confines of the induction device of the station interface 208, which can allow for a smaller or thinner housing 202, and can reduce losses and heat generation. The induction device utilized on the implantable portion 102 is also relatively small, thus, the associated induction device in the remote interface 210 is sized appropriately.

Figure 2B:
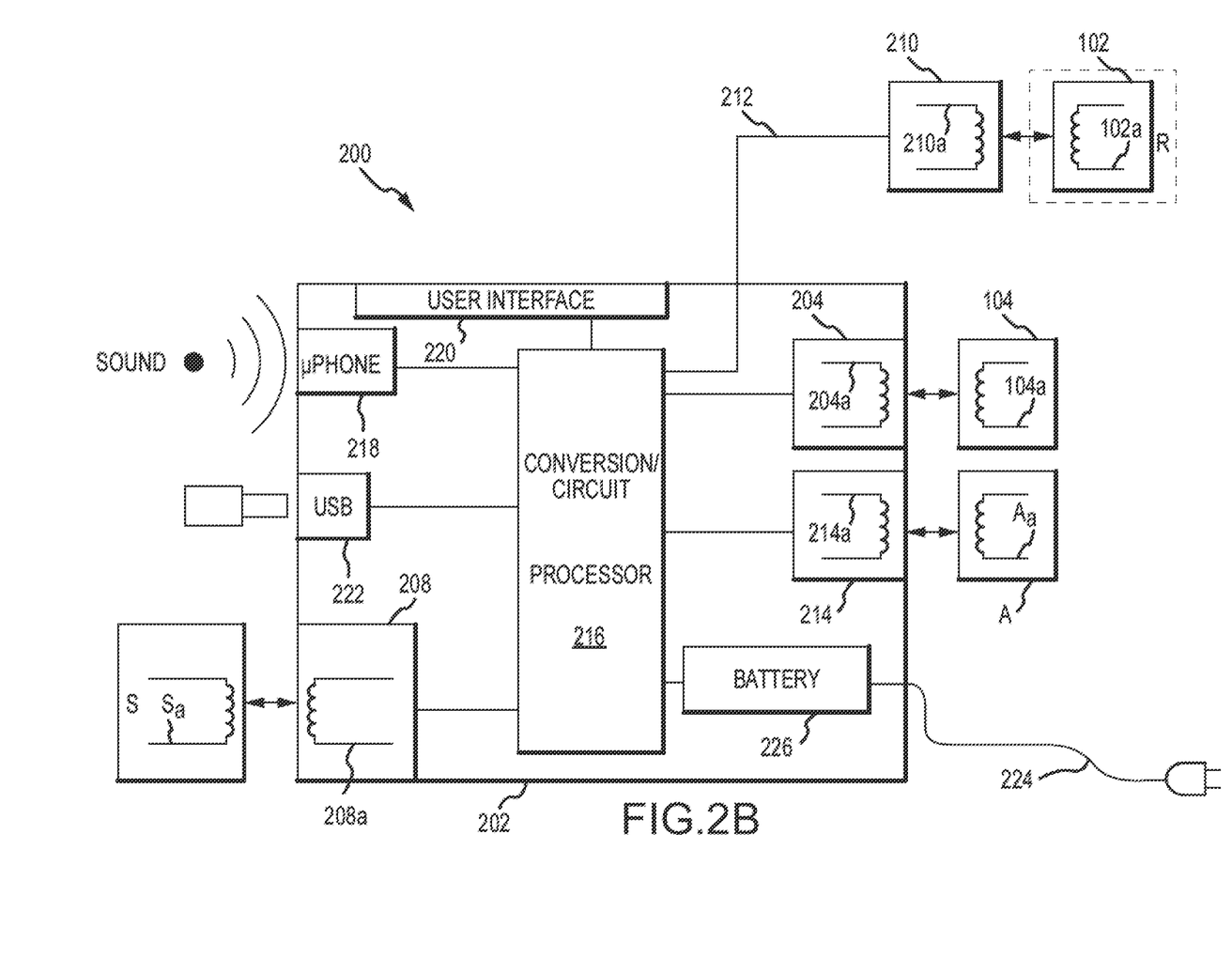
FIG. 2B is a schematic perspective view of another embodiment of a bridge device used to wirelessly charge an auditory prosthesis.

FIG. 2B is a schematic perspective view of another embodiment of a bridge device 200 used to wirelessly charge an auditory prosthesis. Several of the components are described above with regard to FIG. 2A and are not necessarily described further below. The housing 202 includes the portable device interface 204, station interface 208, and remote interface 210, along with their associated induction devices 204a, 208a, 210a, respectively. The associated portable device/external portion 104, station S, and implantable portion 102 (as well as their respective induction devices 104a, Sa, 102a) are also depicted. Additionally, the bridge device 200 can include an accessory interface 214, which includes an accessory induction device 214a. The accessory A, in this case, can be any device generally unrelated to an auditory prosthesis, such as a smart phone, notebook computer, or other device capable of wireless charging or data signal transfer. By including an accessory interface 214, a recipient can charge her auditory prosthesis and her smart phone simultaneously, thus saving time when only a single wireless charging station S is available.

The bridge device 200 also includes a conversion circuit, which in certain embodiments can be incorporated into a processor 216 that converts the incoming signal from the station S to an outgoing signal to the implanted portion 102 and external portion 104 of the auditory prosthesis (and any accessories A). Other peripheral devices can be in communication with the processor 216, so as to increase functionality of the bridge device 200. One or more inputs can be incorporated into the bridge device 200. For example, a microphone 218 can be utilized. When a recipient is charging, e.g., the external portion 104 of their auditory prosthesis, the microphone on the external portion 104 is no longer receiving sound signals, and thus not providing a stimulation signal to the recipient. Accordingly, the microphone 218 can receive sound at the bridge device 200, convert those signals, and send those signals to the implanted portion 102 as required. This allows the recipient to still receive an auditory stimulation during charging procedures. A user interface 220 in the form of one or more buttons, switches, dials, graphic user interface, etc., can also be included. This can allow the recipient to control aspects of charging, adjust settings on their device, etc. For example, in the case of a totally-implantable cochlear implant, settings are adjusted by placing an external portion having volume controls thereon proximate the implantable portion to adjust the volume. With the user interface 220 of the charging bridge 200, volume or other settings could be adjusted while the implantable portion 102 is being charged, since signals related to volume adjustment, as well as other settings, can also be sent via the remote induction device 210a, as described in more detail below. The bridge device 200 can also include a USB port 222 that can be used, for example, for software updates, control settings, or diagnostic purposes. The bridge device 200 can be connected to some type of external power source, typically via a plug connection 224 that can be connected to a building power service, automobile accessory power jack, a computer (via, e.g., a USB connection), etc. A battery 226 can also be included so the bridge device 200 can be utilized in the absence of an external power source. The plug connection 224 can also be used to charge the battery 226. In either case, the conversion circuit/processor 216 converts battery or building power to a wireless charging protocol that can be transmitted to the portable device 104.

Figure 3:
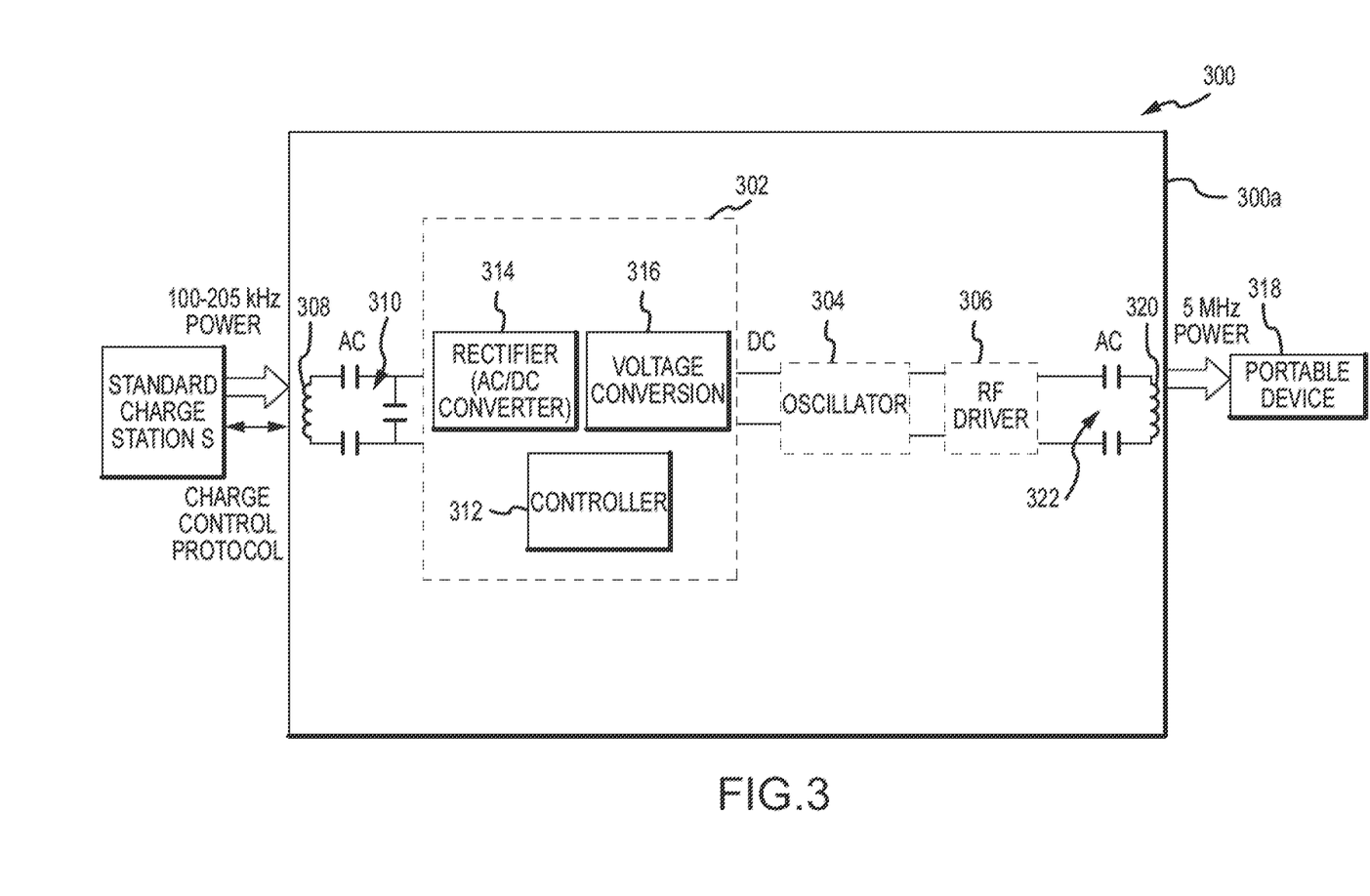
FIGS. 3 and 4 are partial schematic diagrams of a bridge device used to wirelessly charge an auditory prosthesis in accordance with several embodiments.

FIG. 3 is a partial schematic diagram of a conversion circuit 300 used to wirelessly charge an auditory prosthesis in accordance with an embodiment of the technology. The conversion circuit 300 includes, in this embodiment, three integrated circuits, although other configurations are contemplated. Additionally, the various additional components (inputs, etc.) depicted above can also be incorporated into this and the following embodiments. The circuits include a standard wireless charging protocol circuit 302, an oscillator 304, and a radio-frequency (RF) driver 306. In this embodiment, a standard wireless charging protocol, such as the Qi standard, is depicted being delivered to a station induction device 308 from a station S. The Qi standard transmits power at a 100-205 kHz frequency, but other standards using different frequencies can also be utilized, such as those associated with A4WP or PowerMat standards. A set of capacitors 310 are placed in either parallel or series arrangement. Communication and charge control to the charging station S is handled via a load modulation scheme. In another example, A4WP operates at closer to 7 MHz and uses Bluetooth Lower Energy (BTLE) as its backlink control mechanism. The charge control protocol is defined by the standard, sets up the communication link, and controls the charging process. A controller 312 contains the charging intelligence described further herein and controls the power transfer. A rectifier 314 converts the AC current to a DC current, while a voltage converter reduces the incoming signal voltage if it is too high for the portable device 318. A DC current is delivered to the oscillator 304, which can be a custom crystal oscillator or a spread spectrum oscillator normally operating at the desired frequency of the portable device 318, in this example, about 5 MHz frequency. The RF driver 306 is capable of delivering a high current to the portable device induction device 320. Series capacitors 322 are also included. Signal transmission to an implanted portion is similar, although it can be desirable to locate the remote induction device and the RF driver in the remote interface (e.g., remote from the bridge housing 300a) to minimize losses and reduce emissions for electromagnetic compliance associated with the cable.

Figure 4:
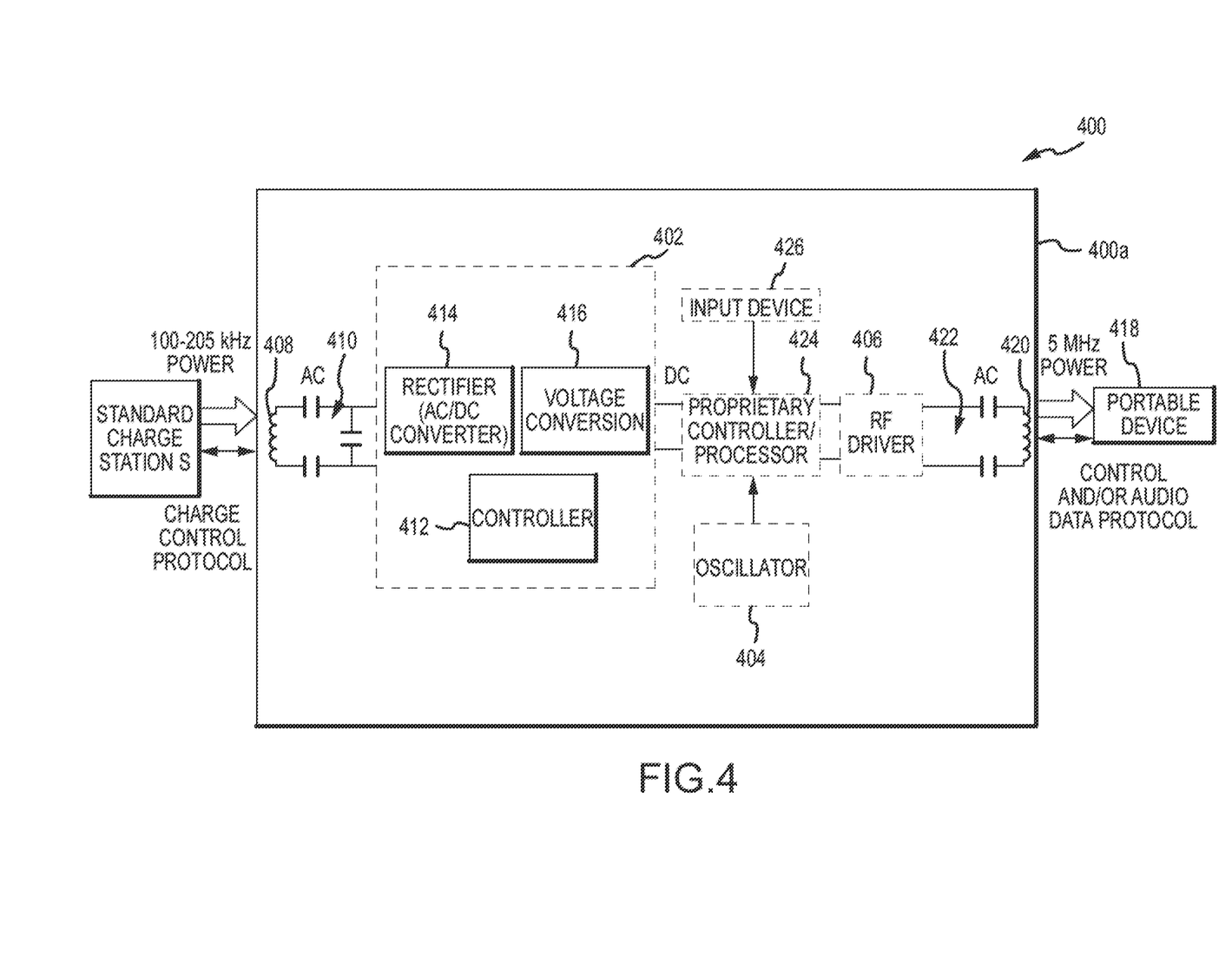

FIG. 4 is a schematic diagram of a bridge device 400 used to wirelessly charge an auditory prosthesis in accordance with another embodiment of the technology. Similar components having similar reference numerals are described above with regard to FIG. 3 and are generally not described further. In addition to transmitting power, a processor 424 can also utilize a communication link to allow the recipient to change volume or other settings while charging their portable device 418. In this embodiment, the charge control process can be controlled externally for a more efficient charging process. Additionally, the bridge device 400 can include an input device 426 such as those described above. For example, if the input device 426 includes volume control, the recipient volume selection is processed by the processor 424 then sent to the portable device 418. A microphone input device, for example, can be utilized to transmit audio data to the recipient while her device is being charged. Various types of data signals can be transmitted, including control data, audio data, volume setting data, classifier setting data, etc.

While exemplary embodiments of bride devices are illustrated in FIGS. 2A and 2B, one of skill in the art will appreciate the bridge device can have many different form factors. For example, the bridge device can have a form factor such as a cell phone cover, a coaster, a flexible or rigid mat, a key fob, rounded shape, square shape, decorative shapes, etc. As such, various different form factors can be employed for the bridge device without departing from the spirit and scope of this disclosure.

Figure 5:
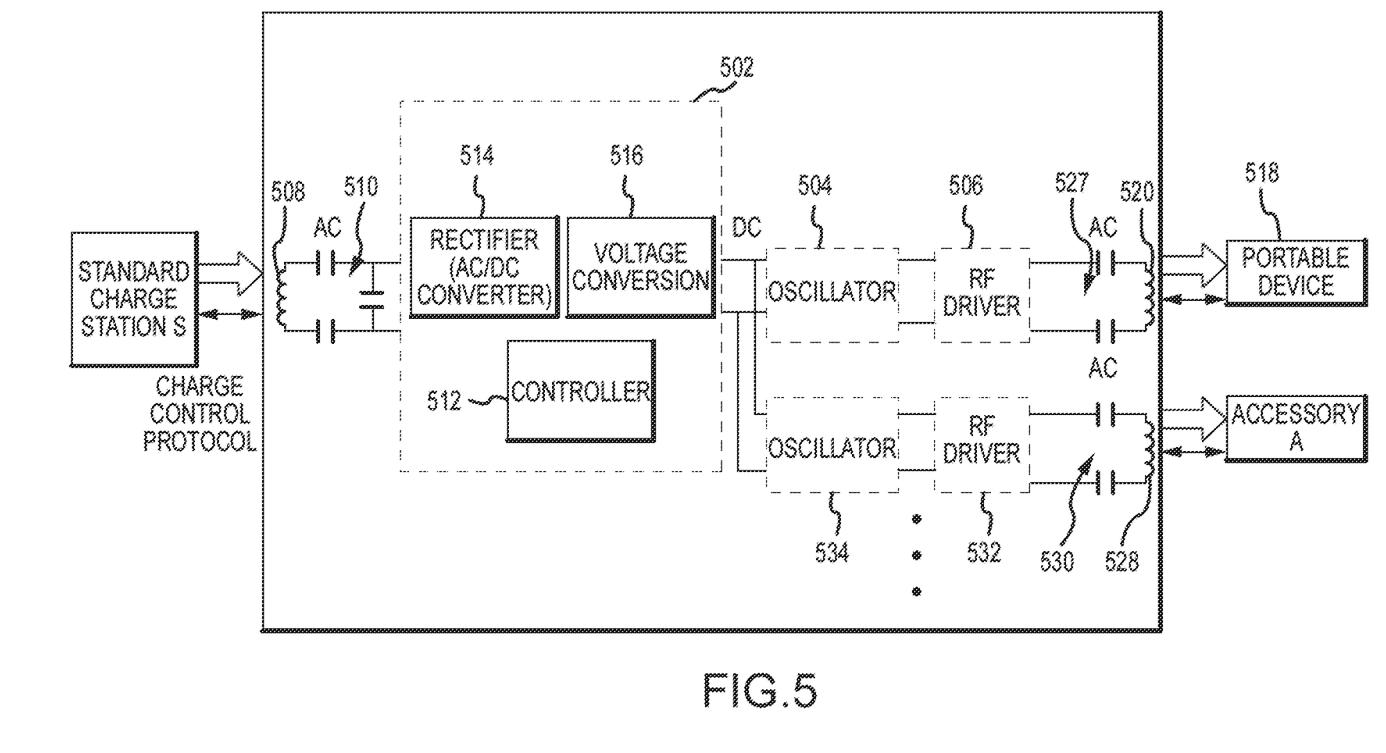
FIG. 5 is a schematic diagram of a bridge device used to wirelessly charge an auditory prosthesis in accordance with another embodiment of the technology.

FIG. 5 is a schematic diagram of a bridge device 500 used to wirelessly charge an auditory prosthesis in accordance with another embodiment of the technology. Similar components having similar reference numerals are described above with regard to FIG. 3 and are generally not described further. In addition to the portable device induction device 520, the depicted bridge device 500 includes an accessory induction device 528 connected to capacitors 530, an RF driver 532, and an oscillator 534 for transmitting power to an accessory A. This embodiment allows the recipient to charge her accessory A (e.g., a smart phone) simultaneously with her portable device 518.

Returning to FIG. 2B, various signals are sent between the bridge device 200 and the portable device 104, remote device 102, accessory A, and starter S. For example, the external portion 104 sends an identification signal to the bridge device 200 by using backlink telemetry pulses or load modulation. The identification signal can include the device identification and authentication information, as well as type of the battery, battery charging history, temperature, and the like. Subsequently, a communication signal is transferred by means of a pulsating or modulated charging signal. Each interface 204, 208, 210, 214 can be hardware, software, or a combination of hardware and software that receives the communication signal. In the depicted embodiment, each interface 204, 208, 210, 214 is hardware. The RF drivers (FIGS. 3-5) send a signal to its associated coil, which transfers power or energy to the associated coil on the device being charged. Signals sent between the bridge device 200 and the external portion 102, implanted portion 102, accessory A, and station S are as described above, and can include a communication signal. Additionally, power or energy is sent from the bridge device 200 as depicted. In certain embodiments, a status signal can be sent from the external portion 104 to the bridge device 200. A predetermined interaction sequence can dictate the type of information sent between the bridge device 200 and the external portions 104 or implanted portion 102. For example, the bridge device 200 can first request or command that particular information to be sent from the external portion 104. In response or reply, the external portion 104 can send the requested information in the identification signal. In another example, a magnetic field sensor can detect the magnetic field generated by the magnet located on the external portion 104 or implanted portion 102. Thus, proximity between the bridge device 200 and external portion 104 or implanted portion 102 is detected and the bridge device 200 sends a communication signal that invokes a status request of the external portion 104 or implanted portions 102 by means of a pulsating or modulated charging signal.

Figure 6:
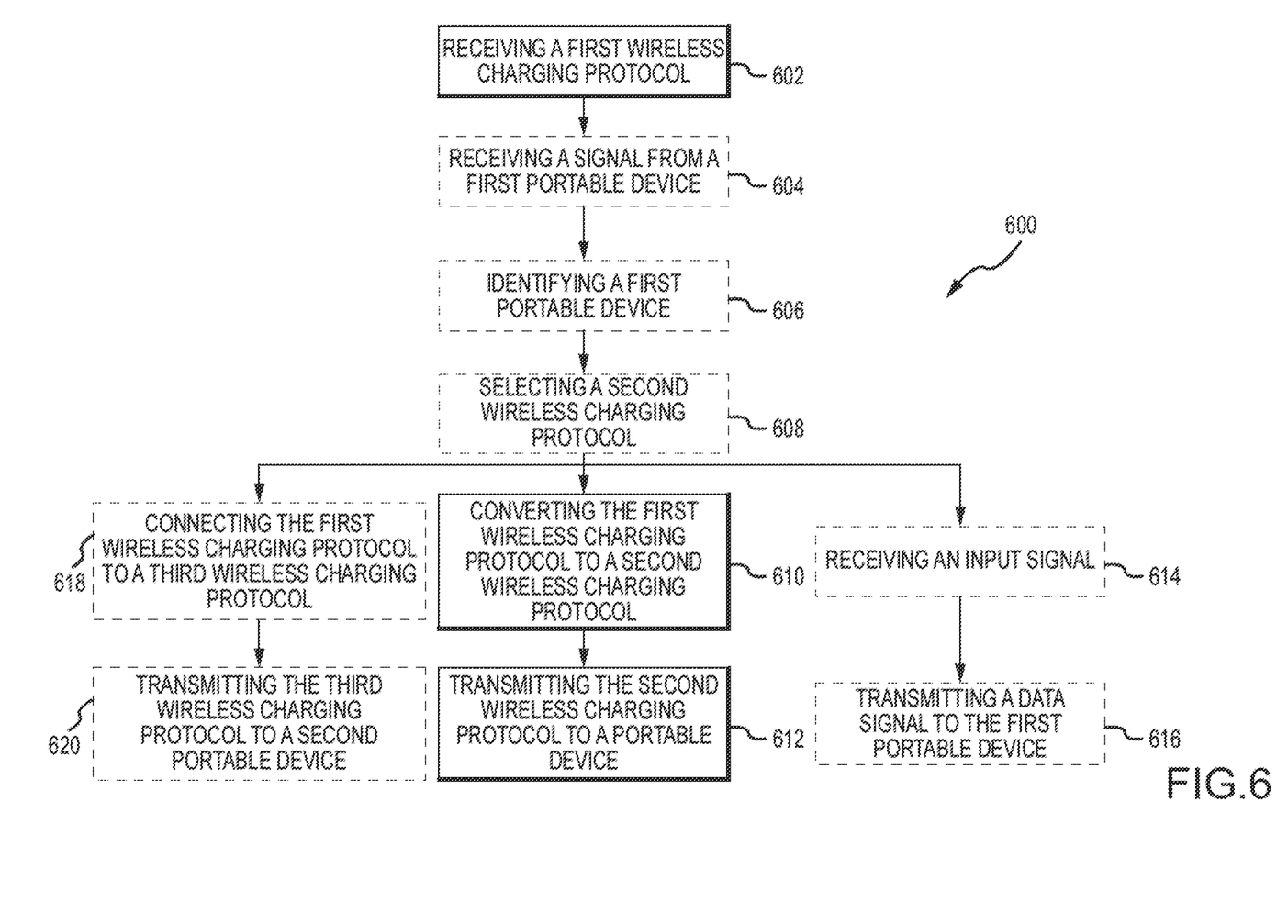
FIG. 6 is a method of transmitting signals to an auditory prosthesis via a bridge device.

FIG. 6 is a method 600 of transmitting signals to an auditory prosthesis via a bridge device. The method 600 begins by receiving a first wireless charging protocol from a charging station, operation 602. The first wireless charging protocol can be a standard charging protocol such as the Qi standard, which transmits power at a 100-205 kHz frequency. Other standards using different frequencies can also be utilized, such as those associated with A4WP or PowerMat standards. The first wireless charging protocol utilizes a first frequency. For example, the Qi standard transmits power at a frequency of 100-250 kHz, while the A4WP standard transmits power at a frequency of 7 MHz. The bridge device can be manufactured to be operable with more than one standard protocol. Depending on the functionality of the bridge device, the bridge device can receive a signal from a first portable device, operation 604. This signal can allow the bridge device to identify the first portable device, operation 606. The identification can include portable device type and/or manufacturer, required charging protocol, battery life remaining, or other criteria. If the bridge device is capable of converting the incoming first wireless charging protocol to one of a plurality of wireless charging protocols, the appropriate second wireless charging protocol can be selected based on the received signal, operation 608. The bridge device then converts the first wireless charging protocol to a second wireless charging protocol, operation 610, which can have a frequency different than that of the first wireless charging protocol. For example, the second wireless charging protocol can be a proprietary wireless charging protocol utilized by a medical device manufacture across a family of products or a specific product. In an embodiment, the second wireless charging protocol is proprietary to Cochlear Ltd. of Australia, and is used in conjunction with auditory prostheses manufactured by that company. The Cochlear Ltd. wireless protocol utilizes a frequency of about 5 MHz. Once converted, the second wireless charging protocol can be transmitted to the portable device by the bridge device, operation 612, until the portable device is charged or some other condition occurs.

Other operations can be performed simultaneously or sequentially by the bridge device. For example, if the bridge device includes an input, an input signal can be received, operation 614. Various inputs are described above. A signal related to the input (e.g., volume, settings, etc.) can be sent to the first portable device, operation 616. Additionally, the bridge device can also charge additional devices or accessories, if so configured. The first wireless charging protocol can be converted into a third wireless charging protocol, operation 618, for charging an accessory (e.g., a device unrelated to the auditory prosthesis). After conversion, the third wireless charging protocol can be transmitted to the accessory, operation 620. In certain embodiments, the first and third wireless charging protocols can be substantially similar.

Figure 7:
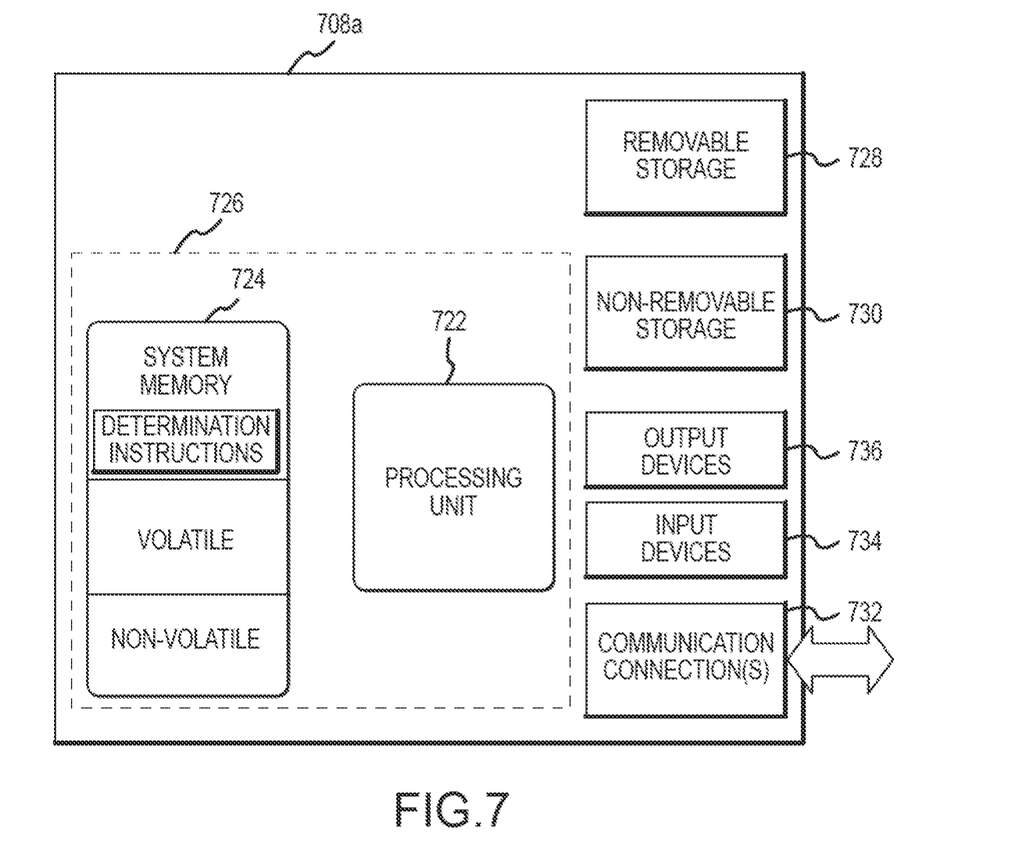
FIG. 7 illustrates one embodiment of a suitable operating environment in which one or more of the present embodiments can be implemented.

FIG. 7 illustrates one embodiment of a suitable operating environment 708 in which one or more of the present embodiments can be implemented. This is only one example of a suitable operating environment and is not intended to suggest any limitation as to the scope of use or functionality. Other well-known computing systems, environments, and/or configurations that can be suitable for use include, but are not limited to, personal computers, server computers, handheld or laptop devices, multiprocessor systems, microprocessor-based systems, programmable consumer electronics such as smart phones, network PCs, minicomputers, mainframe computers, smartphones, tablets, distributed computing environments that include any of the above systems or devices, and the like.

In its most basic configuration, operating environment 708 typically includes at least one processing unit 722 and memory 724. Depending on the exact configuration and type of computing device, memory 724 (storing, among other things, instructions to perform the device identification, signal conversion, and charging methods described herein) can be volatile (such as RAM), non-volatile (such as ROM, flash memory, etc.), or some combination of the two. This most basic configuration is illustrated in FIG. 7 by line 726. Further, environment 708 can also include storage devices (removable, 728, and/or non-removable, 730) including, but not limited to, magnetic or optical disks or tape. Similarly, environment 708 can also have input device(s) 734 such as touch screens, keyboard, mouse, pen, voice input, etc. and/or output device(s) 736 such as a display, speakers, printer, etc. Also included in the environment can be one or more communication connections, 732, such as LAN, WAN, point to point, Bluetooth, RF, etc.

Operating environment 708 typically includes at least some form of computer readable media. Computer readable media can be any available media that can be accessed by processing unit 722 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 708 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein comprise such modules or instructions executable by computer system 708 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 708 is part of a network that stores data in remote storage media for use by the computer system 708.

The embodiments described herein can be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices can be employed to perform the functionality disclosed herein without departing from the scope of the disclosure.

Although specific embodiments were described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. An apparatus comprising:
   a housing;
   a first induction device disposed in the housing, the first induction device for receiving a first wireless charging protocol having a first frequency;

a second induction device disposed in the housing, the second induction device for transmitting a second wireless charging protocol having a second frequency, wherein the second induction device is disposed within an outer perimeter of the first induction device; and a conversion circuit operably connected to the first induction device and the second induction device for converting the first wireless charging protocol to the second wireless charging protocol.

2. The apparatus of claim 1, further comprising a third induction device disposed remote from the housing and connected to the conversion circuit with a cable, wherein the third induction device is configured to receive power over the cable.

3. The apparatus of claim 1, wherein the first induction device comprises a receiver coil and the second induction device comprises a transmitter coil.

4. The apparatus of claim 1, wherein the second induction device comprises a plurality of second induction devices.

5. The apparatus of claim 1, further comprising at least one of a battery and a power cable.

6. The apparatus of claim 1, further comprising an input disposed on the housing.

7. The apparatus of claim 6, wherein the input comprises at least one of a microphone, a button, a switch, a port, and a graphic user interface.

8. The apparatus of claim 1, wherein the first induction device is a receiver induction device and the second induction device is a transmitter induction device.

9. A method comprising:
receiving, at a first induction device from a wireless charger device, a first wireless charging protocol having a first frequency;
converting the first wireless charging protocol to a second wireless charging protocol having a second frequency; and
transmitting, from a second induction device that surrounds the first induction device, to a first portable device, the second wireless charging protocol.

10. The method of claim 9, further comprising:
identifying the first portable device; and
selecting the second wireless charging protocol based at least in part on the identified first portable device.

11. The method of claim 10, wherein the identifying operation comprises receiving a signal from the first portable device.

12. The method of claim 9, further comprising receiving an input signal.

13. The method of claim 12, further comprising transmitting a data signal to the first portable device based at least in part on the input signal.

14. The method of claim 12, further comprising:
converting the first wireless charging protocol to a third wireless charging protocol having a third frequency; and
transmitting, to a third portable device, the third wireless charging protocol.

15. The method of claim 14, wherein the third wireless charging protocol is similar to the first wireless charging protocol.

16. The method of claim 14, wherein transmitting the second wireless charging protocol to the first portable device and transmitting the third wireless charging protocol to the second portable device occurs simultaneously.

17. An apparatus comprising:
a first device for receiving a first wireless charging protocol;
a conversion circuit for converting the first charging protocol into a second wireless charging protocol; and
a second device surrounding the first device for transmitting the second wireless charging protocol.

18. The apparatus of claim 17, wherein the first wireless charging protocol is based at least in part on energy received from an induction device, a battery, and a building power source.

19. The apparatus of claim 17, wherein the first device and the second device each comprise coils.

* * * * *